United States Patent [19]
Ishii et al.

[11] Patent Number: 5,302,654
[45] Date of Patent: Apr. 12, 1994

[54] PRODUCTION OF POLYMER MICROPARTICLES HAVING WATER-INSOLUBLE CHEMICALS IMMOBILIZED THEREIN

[75] Inventors: Keizo Ishii, Ashiya; Hidetsumu Okada, Takahama; Masanori Oiwa, Toyonaka; Hisaichi Muramoto, Hirakata; Shinichi Ishikura, Tanabe, all of Japan

[73] Assignee: Nippon Paint Co., Ltd., Osaka, Japan

[21] Appl. No.: 24,966

[22] Filed: Mar. 2, 1993

[30] Foreign Application Priority Data

Mar. 2, 1992 [JP] Japan .................................. 4-81718

[51] Int. Cl.$^5$ .......................... C08F 2/22; C09D 11/02
[52] U.S. Cl. .................................... 524/458; 524/460; 523/160; 523/161; 523/205; 523/211
[58] Field of Search ............... 523/160, 161, 200, 202, 523/205, 206, 210, 211, 223; 524/458, 460

[56] References Cited

U.S. PATENT DOCUMENTS 4,592,990  1/1986  Takagi et al. ........................ 524/460
4,665,107  5/1987  Micale ................................. 523/205

FOREIGN PATENT DOCUMENTS 0246814  11/1987  European Pat. Off. ............ 524/458
2-40105   9/1990  Japan .................................. 524/460

Primary Examiner—Paul R. Michl
Attorney, Agent, or Firm—Millen, White, Zelano & Branigan

[57] ABSTRACT

Polymer microparticles having immobilized therein a water-insoluble substance such as oil-soluble dyes or pigments are produced by a method which includes the steps of forming droplets of a solution of a self-emulsifiable resin in a nonaqueous solvent containing the water-insoluble substance and an ethylenically unsaturated monomer suspended in an aqueous medium, and then allowing the monomer in the droplets to polymerize in situ.

20 Claims, No Drawings

PRODUCTION OF POLYMER MICROPARTICLES HAVING WATER-INSOLUBLE CHEMICALS IMMOBILIZED THEREIN

FIELD OF THE INVENTION

This invention generally relates to the production of polymer microparticles having immobilized therein a hydrophobic substance, especially those polymer microparticles which include oil-soluble dyes or pigments for use in water-based inks.

BACKGROUND OF THE INVENTION

Heretofore water-based inks used in various writing intruments such as founting pens, felt pens, or draftman's pens as well as those used in ink-jet plotter or printer machines for information recording purposes have the conventionally contained a water-soluble dye. Such water-based inks containing water-soluble dyes, however, have the defect that when writing or printing with such inks, letters or printed objects may often become blurred. Furthermore, they are not water-resistant and durable even after drying. Japanese Kokai (laid open) Patent Application No. 172076/87 discloses a water-based ink produced by adding an oil-soluble dye dissolved in an organic solvent to an aqueous suspension of a water-insoluble polymer, and allowing the oil-soluble dye to diffuse into the polymer particles. According to this technique, however, it is not possible for the polymer particles to carry an amount of dyes desirable for imparting the ink with optimal chromatic parameters. This is because the diffusion coefficient of particular dyes is the limiting factor. Japanese Kokai (laid open) Patent Application No. 273274/87 proposes a water-based ink employing pigments as a colorant. This ink comprises a polymer dispersion produced by emulsion polymerizing monomers in the presence of a protective colloid but the polymer particles themselves are discrete from the pigment particles. Thus, they are susceptible to phase separation upon storage.

A need exists for a water-based ink which eliminates or ameliorates various defects of the prior art water-based inks noted as above.

SUMMARY OF THE INVENTION

According to the present invention, polymer microparticles having immobilized therein a water-insoluble substance such as oil-soluble dyes or pigments are provided. The polymer microparticles are produced by preparing a solution of a self-emulsifiable resin in a non-aqueous solvent, dissolving or dispersing an oil soluble dye or pigment in said solution, emulsifying said solution in conjunction with an ethylenically unsaturated monomer or a mixture thereof into droplets suspended in an aqueous medium, and allowing said ethylenically unsaturated monomer to polymerize in situ.

According to this method, the amount of colorant to be carried by the polymer microparticles may be increased as desired. When the self-emulsifiable resin also has an ethylenically unsaturated function in the molecule, a cross-linking reaction takes place with the ethylenically unsaturated monomer so that the physical and chemical stability of the polymer particles are greatly increased.

The disclosed method is useful to immobilize not only oil-soluble dyes or pigments but also other water-insoluble substances such as medical drugs, pesticides, catalysts and the like for use as a substitute for well-known microcapsules.

DETAILED DESCRIPTION OF THE PREFERRED EMBODIMENT

The self-emulsifiable polymers or resins are known in the art and may be produced by introducing an ionizable or non-ionizable hydrophilic group or block into a hydrophobic polymer or resin such as acrylic, epoxy, polyester, poly(styrene-maleic anhydride), maleinized polyalkadiene, polyurethane and aminoplast resins. The hydrophilic group or blocks may be of anionic (e.g. carboxylic or sulfonic acid group), cationic (e.g. amino or quaternary ammonium group), or nonionic (e.g. polyoxyethylene block).

Self-emulsifiable acrylic polymers may be produced by copolymerizing a carboxyl group-containing monomer (e.g. acrylic, methacrylic, maleic, cinnamic or crotonic acid), a sulfonic group-containing monomer (e.g. sulfoethyl metacrylate, 2-acrylamide-2-methylpropane sulfonic acid, vinylsulfonic acid or stylene sulfonic acid), an amino group-containing monomer (e.g. dimethylaminoethyl methacrylate or N-dimethylaminopropylacrylamide), or a polyoxyethylene block-containing monomer (e.g. polyethylene glycol monomethacrylate) with a hydrophobic comonomer such as alkyl acrylate or methacrylates (e.g. methyl, ethyl, propyl, butyl, hexyl or lauryl), styrene or its derivatives (e.g. styrene, methylstyrene or chloromethylstyrene) or the like.

Self-emulsifiable epoxy resins may be produced, for example, by ring-opening at least a portion of the epoxide rings possessed by the conventional bisphenol type epoxy resins with a compound capable of introducing a basic, acidic, nonionic or amphoionic hydrophilic group. Inherently self-emulsifiable epoxy resins may be used as such.

Self-emulsifiable polyesters may be prepared by reacting a polybasic acid component and a polyol component at an appropriate ratio to produce a carboxyl group-terminated polyester.

Self-emulsifiable polyalkadiene resins may be produced by reacting a polyalkadiene polymer with a ethylenically unsaturated dicarboxylic acid (e.g. maleic anhydride, himic anhydride, fumaric acid and itaconic acid) according to the Diels-Adler reaction.

Self-emulsifiable polyurethane polymers may be produced by reacting an organic polyisocyanate (e.g. hexamethylenedi -isocyanate, tolylenediisocyanate, 4,4'-diphenylmethanediiso-cyanate, xylylenediisocyanate and isophoronediisocyanate) with a polyether polyol containing a polyoxyethylene block.

Self-emulsifiable aminoplast resins include urea-formaldehyde resins, melamine-formaldehyde resins or their etherified products with a lower alkanol such as methanol or butanol.

The self-emulsifiable polymers or resins may have a cross-linkable ethylenic function. Such polymer or resins may be produced by reaction a polymer or resin having a functional group such as hydroxyl, carboxyl, acid anhydride, amino or epoxy group with an ethylenic monomer having another functional group reactive with the first-mentioned functional group. For example, a hydroxyl group-containing polymer may be reacted with maleic anhydride to produce a half ester having a free carboxyl group and an ethylenic unsaturation. Styrene-maleic anhydride copolymers may be reacted with a hydroxy group-containing monomer such as 2- hydroxyethyl methacrylate to open the acid anhydride ring into a maleic acid half ester structure having a cross-linkable site. Maleinized polybutadienes may be reacted with a polyethylene glycol derivative (e.g. esters with fatty acids, ethers with alkylphenols or fatty alcohols) to introduce both carboxyl group and polyoxyethylene block using the ring-opening reaction of their acid anhydride ring with the polyethylene glycol derivative. Similarly, polymers or resins having an epoxy, carboxyl or amino function may be reacted with an acrylic monomer having a carboxyl, epoxy or isocyanate group to introduce the cross-linkable ethylenic function.

The self-emulsifiable polymers or resins preferable have an number average molecular weight from 1,000 to 100,000. In addition, they generally have a water tolerance greater than 4 and a surface tension less than 51 dyne/cm at a concentration of 1% by weight in a nonaqueous solvent. If the water tolerance is too small it is difficult to emulsify the resin solution in an aqueous medium or the resulting emulsion particles become too large. Similarly, if the surface tension is too large, it is difficult to disperse the resin solution as droplets in an aqueous medium.

The self-emulsifiable polymers or resins are nuetralized at least partially with a base (e.g. ammonia, mono- or trimethylamine, dimethylethanolamine, morpholine, sodium hydroxide, potassium hydroxide or lithium hydroxide) when they are acidic polymers, or an acid (e.g. hydrochloric, sulfuric, nitric, acetic, formic, or lactic acid) when they are basic polymers.

Examples of monomers to be polymerized in situ include monofunctional monomers such as alkyl acrylate or methacrylate, styrene or styrene derivatives as exemplified above, or polyfunctional monomers such as ethylene glycol di(meth)acrylate, diethylene glycol di(meth)acrylate, 1,3-propanediol di(meth)acrylate, 1,4-butanediol di(meth)-acrylate, neopentyl glycol di(meth)acrylate, trimethylpropane tri(meth)acrylate, glycerin tri(meth)-acrylate, diallyl phthalate, triallyl trimellitate or divinylbenzene, or a mixture of monofunctional and polyfunctional monomers.

Any oil-soluble or water-insoluble dye or pigment may be used as colorants. For use in the preparation of water-based inks, at least black, yellow, red and blue dyes or pigments are required.

In order to produce polymer microparticles carrying the colorant, the self-emulsifiable polymer or resin is dissolved in a nonaqueous solvent. Examples of usable nonaqueous solvents include alcohols (e.g. methanol, ethanol, propanol, butanol and 2-ethylhexanol), ethylene glycol monoalkyl ethers (e.g. methyl, ethyl and butyl ethers), acetate esters (e.g. methyl and ethyl esters), ketones (e.g. methyl ethyl ketone and methyl isobutyl ketone), aromatic hydrocarbons (e.g. benzene, toluene and xylene), aliphatic hydrocarbons (e.g. hexane and octane), and mixtures of these solvents. To this solution is then added an amount of the colorant sufficient to achieve the desired color density. The colorant may be added in such a large amount even up to 50% by weight of the polymer particles. The monomer may also be added to the resin solution before the emulsifying step or it may preferably be added to the emulsion of the colorant-containing resin solution to make droplets having the monomer diffused therein. The amount of the monomer preferable lies between 5% and 20% by the combined weight of the resin as solids and the monomer.

The in situ polymerization of the monomer may be initiated by incorporating into the resin solution droplets of an oil-soluble initiator such as benzoyl peroxide, p-chlorobenzoyl peroxide, lauroyl peroxide, t-butylperoxy benzoate, azobisisobutyronitrile, 2,2'-azobis(2-methylbutyronitriel), 2,2'-azobis(2,4-dimethylvaleronitrile) or the like, or adding to the aqueous phase of the emulsion a water-soluble initiator such as potassium persulfate, ammonium persulfate, 4,4'-azobis(4-cyanovaleric acid), 2,2'-azobis(2-methylpropionamidine) or the like. The particle size may be controlled within a range between 0.01 and 1 micron by selecting the polymerization condition or a suitable dispersant. Generally, the emulsion polymerization method using a water-soluble initiator dissolved in the aqueous phase gives finer particle sizes. After the polymerization reaction, the polymer microparticles may be isolated from their suspension by the conventional methods such as freeze-drying, spray drying, solvent substitution or the like. For use as a water-based ink, the polymer particles are resuspended in another aqueous medium with conventional ink additives.

The present invention is useful not only for immobilizing water-insoluble dyes or pigments but also it finds use for immobilizing other water-insoluble substances for controlling their release rate or availability. In this sense, the polymer microparticles of the present invention may be used as a substitute for the well-known microcapsules. Since the polymer microparticles of the present invention are not soluble in water or conventional organic solvents and since their particle size is generally less than the particle size of microcapsules, the present invention is useful to immobilize a variety of chemicals to be added to coating compositions. Examples such chemicals include bacteriocides, fungicides, insecticides, antifouling agents, anti-algal agents, repellents and other pesticides. For example, polymer microparticles carrying a trialkyltin compound are useful as a sustained release antifouling agent to be added antifouling paints. Many coating compositions include a catalyst which promotes the curing or cross-linking reaction of their vehicle resins. Various organometallic compounds catalyzing the cross-linking reaction with a polyisocyanate compound and the oxidation polymerization reaction of oil-modified alkyd resins are typical examples thereof. The catalyst remains in the cured film even after having performed its function and often adversely affects the weatherability of the film. Such adverse affects may be avoided by immobilizing the catalyst according to the present invention. Other examples of additives include antioxidants such as hindered pheno and UV absorbers such as TINUVIN B (a trademark of Ciba-Geigy; see *Merck Index*, 11th Ed., monograph no. 9381).

The following examples are offered for illustrative purposes only. All parts and percents therein are by weight unless otherwise indicated.

EXAMPLE 1

A reactor equipped with a stirrer, heater and reflux condenser was charged with 300 parts of a styrene-maleic anhydride copolymer (SMA 3000 sold by Atochem Inc.), 0.89 parts of p-methoxyphenol and 1.78 parts of dimethylbenzylamine. After heating the mixture to 125° C. with stirring, 27.5 parts of n-butanol were added dropwise over 30 minutes and allowed to react for additional 1 hour. Then 19.0 parts of 2-hydroxyethyl methacrylate were added dropwise to the reactor and allowed to react for additional 30 minutes. The resulting resin was found to have a number average molecular weight of 4.790 according to the GPC method and an acid number of 148.

56 parts of the resulting resin varnish were diluted with 14 parts of a 1:1 mixture of benzene and ethanol. Then 7 parts of nigrosine were dispersed therein. To this were added 4 parts of dimethylethanolamine and 450 parts of deionized water gradually with stirring to make an emulsion. After the addition of 26 parts of methyl methacrylate, the emulsion was stirred again vigorously, transferred to another reactor and heated to 80° C. Then an initiator solution containing 0.7 parts of azobiscyanovaleric acid and 0.4 parts of dimethylethanolamine dissolved in 10 parts of deionized water was added dropwise to the emulsion over 1 hour with stirring. The mixture was allowed to react for additional 2 hours, cooled to room temperature and filtered through a 400 mesh filter to remove large agglomerates. An emulsion of black polymer microparticles having a mean particle size of 250 microns was obtained. 11.1% solids.

EXAMPLE 2

The same reactor as used in Example 1 was charged with 44.0 parts of methylcellosolve and heated to 120° C. with stirring. To this was added dropwise a mixture consisting of 30.0 parts of styrene, 35.0 parts of methyl methacrylate, 20.5 parts of lauryl methacrylate, 6.0 parts of glycidyl methacrylate, 3.0 parts of sulfoethyl methacrylate and 2.0 parts of azobisbutyronitrile over 3 hours and allowed to react for additional 2 hours. After the reaction, 7.0 parts of maleic acid were added and allowed to react at 130° C. for 2 hours. The resulting resin was found to have a number average molecular weight of 8.600 according to the GPC method and an acid number of 85.

30.0 parts of this resin varnish were taken in a beaker and 3.0 parts of Diaresin Blue(Mitsubishi Kasei Corporation) were dissolved therein. Then the resin varnish was emulsified in 340 parts of deionized water. To this were added 11.8 parts of styrene, 5 parts of ethylene glycol dimethacrylate and 0.2 parts of azobisdimethylvalero nitrile followed by vigorous stirring. The emulsion was transferred to another reactor, allowed to react at 70° C. for 6 hours with stirring, cooled to room temperature and filtered through a 400 mesh filter to remove large agglomerates. An emulsion of blue polymer microparticles having a mean particle size of 213 microns was obtained. 8.8% solids.

EXAMPLE 3

A reactor equipped with a stirrer, thermometer, reflux condenser and nitrogen gas tube was charged with polybutadiene (LIR-300 sold by Kuraray Co., Ltd., M.W. about 45,000), 50 parts of xylene, 30 parts of maleic anhydride and 1 part of N-phenyl-N'-(2,3-dimethylbutyl) -p-phenylenediamine (Nocrac 6C sold by Ouchi Shinko Kagaku Kogyo K. K.). The mixture was allowed to react at 190° C. for 6 hours under the nitrogen gas current to produce maleinized polybutadiene polymer. To the reactor were added 26 parts of ethylene glycol monobutyl ether, 58 parts of polyethylene glycol monolauryl ether (Emulgen 109P sold by Kao Corporation), 3 parts of N,N-dimethylbenzylamine and 330 parts of xylene. The mixture was allowed to react at 130° C. for 30 minutes whereupon a resin solution having a solids content of 60% was obtained. The resin was found to have a number average molecular weight of 56,000 according to the GPC method and an acid number of 38.

56 parts of this resin varnish was diluted with 4 parts of toluene and 3 parts of butanol and then 7 parts of Diaresin Red S (Mitsubishi Kasei Corporation) were dispersed in the resin solution. To this were added 2.24 parts of dimethylethanolamine and 450 parts of deionized water to produce an emulsion. Then 16 parts of styrene and 10 parts of divinylbenzene were added to the emulsion with vigorous stirring. This emulsion was transferred to another reactor and heated to 80° C. To this was added dropwise an initiator solution of 0.7 parts of azobiscyanovaleric acid in 10 parts of deionized water containing 0.4 parts of dimethylethanolamine over 1 hour followed by reacting for additional 2 hours. After cooling to room temperature, the emulsion was filtered through a 400 mesh filter to remove large agglomerates to obtain an emulsion of red polymer particles having a mean particle size of 290 microns. 10.2% solids.

EXAMPLE 4

The same reactor as used in Example 1 was charged with 900 parts of an epoxy resin (EPIKOTE 1001 sold by Yuka Shell Epoxy K. K.) dissolved in 600 parts of dimethylformamide. After the addition of 122 parts of ethanolamine, the mixture was allowed to react at 120° C. for 30 minutes. To this were added dropwise 222 parts of methacryloylisocyanate over 30 minutes followed by reacting for an additional 1 hour. The resulting resin was found to have an average molecular weight of 1430.

56 parts of the resulting resin varnish was diluted with 7 parts of methyl isobutyl ketone and 7 parts of Diaresin Yellow 3G (Mitsubishi Kasei Corporation) were dispersed therein. Then the resin varnish was emulsified in 550 parts of deionized water. To the emulsion were added 16 parts of methyl methacrylate and 10 parts of ethylene glycol dimethacrylate followed by vigorous stirring. To the emulsion transferred in another reactor was added dropwise an initiator solution of 1.0 parts of azobismethylpropionylamidine hydrochloride (V-50 sold by Wako Pure Chemical Industires, Ltd.) in 10 parts of deionized water over 1 hour. The mixture was allowed to react at 80° C. for additional 2 hours, cooled to room temperature and filtered through a 400 mesh filter to remove large agglomerates whereupon an emulsion of yellow polymer microparticles having a mean particle size of 164 micron was obtained. 10.1% solids.

EXAMPLE 5

The emulsion produced in Example 1 was freeze-dried to isolate the polymer microparticles. 7 parts of the polymer particles were dispersed in 93 parts of a 7:3 mixture of ethanol and water and filtered through a 400 mesh filter to remove large agglomerates. The resulting water-based ink was filled into a conventional felt-tip marker pen.

As a control, an ink was prepared by dissolving 0.8 parts of Aizen Spolon BH Special (a water-soluble black dye sold by Hodogaya Chemical Co., Ltd.) and 6.1 parts of polyvinylbutyral resin in 93 parts of ethanol and then filled into a similar marker pen.

An enamelled white board was marked with the inventive ink and the control ink, respectively and the inked areas were allowed to dry completely. Then the inked areas were wiped away with a conventional wiper by reciprocating three times at a wiping load of 200 g. The marked area with the inventive ink was cleaned completely without trace, whereas the control ink remained on the board as a pale trace.

We claim:

1. A method of the production of polymer microparticles having immobilized therein a water-insoluble substance which comprises the steps of:
   dissolving a self-emulsifiable resin having an ethylenically unsaturated group in a nonaqueous solvent;
   dissolving or dispersing said water-insoluble substance in the resulting resin solution;
   emulsifying said resin solution in conjunction with an ethylenically unsaturated monomer or a mixture therof into droplets suspended in an aqueous medium; and
   allowing said monomer to polymerize in said droplets in situ .

2. The method according to claim 1, wherein said water-insoluble substance is a water-insoluble dye.

3. The method according to claim 1, wherein said water-insoluble substance is a pigment.

4. The method according to claim 1, wherein said water-insoluble substance is a water-insoluble pesticide.

5. The method according to claim 1, wherein said water-insoluble substance is an agent which enhances the weatherability of coating films.

6. The method according to claim 1, wherein said water-insoluble substance is an organometallic compound which catalyzes the curing reaction of a vehicle resin of coating compopsitions.

7. The method according to claim 1, wherein said self-emulsifiable resin has an number average molecular weight from 1,000 to 100,000; a water tolerance greater than 4 and a surface tension less than 51 dyne/cm at a concentration of 1% by weight in a nonaqueous solvent.

8. The method according to claim 1, wherein said ethylenically unsaturated monomer is monofunctional.

9. The method according to claim 1, wherein said ethylenically unsaturated monomer is polyfunctional.

10. The method according to claim 1, wherein said ethylenically unsaturated monomer is a mixture of a monofunctional monomer and a polyfunctional monomer.

11. The method according to claim 1, wherein said self-emulsifiable resin is a modified acrylic, epoxy, polyester, styrene-maleic anhydride copolymer, maleinized polyalkadiene, polyurethane or an aminoplast resin having an ionizable group or a polyoxyethylene block.

12. Polymer microparticles of a mean particle size from 0.01 to 1 micron produced by the method of claim 2.

13. Polymer microparticles of a mean particle size from 0.01 to 1 micron produced by the method of claim 3.

14. Polymer microparticles of a mean particle size from 0.01 to 1 micron produced by the method of claim 4.

15. Polymer microparticles of a mean particle size from 0.01 to 1 micron produced by the method of claim 5.

16. Polymer microparticles of a mean particle size from 0.01 to 1 micron produced by the method of claim 6.

17. The method according to claim 1, wherein the thus produced microparticles have a mean particle size from 164 to 290 microns.

18. The method according to claim 1, wherein the monomer which is polymerized in situ is a monofunctional monomer selected from the group consisting of alkyl acrylates, alkylmethacrylates, styrene and its derivatives, a polyfunctional monomer selected from the group consisting of ethylene glycol di(meth)acrylate, diethylene glycol di(meth)acrylate, 1,3-propanediol di(meth)acrylate, 1,4-butanediol di(meth)acrylate, neopentyl glycol di(meth)acrylate, trimethylpropane tri(meth)acrylate, glycerin tri(meth)acrylate, diallyl phthalate, triallyl trimellitate and divinylbenezene, or a mixture of a said monofunctional monomer and said difunctional monomer.

19. An emulsion of oil soluble or water insoluble dye or pigment-containing polymer microparticles, produced according to the method to claim 1.

20. Oil soluble or water insoluble dye or pigment-containing polymer microparticles produced according to the method of claim 1 and thereafter separated from the suspension in which they were produced.

* * * * *